(12) United States Patent
Fishel et al.

(10) Patent No.: US 11,154,706 B1
(45) Date of Patent: Oct. 26, 2021

(54) PILL PACEMAKER WITH BI-V PACING, DDD PACING AND AAI WITH DDD BACKUP PACING

(71) Applicant: NewPace Ltd., Caesarea (IL)

(72) Inventors: Robert Fishel, Delray Beach, FL (US); Gera Strommer, Haifa (IL)

(73) Assignee: NewPace Ltd., Caesarea (IL)

( * ) Notice: Subject to any disclaimer, the term of this patent is extended or adjusted under 35 U.S.C. 154(b) by 432 days.

(21) Appl. No.: 16/260,777

(22) Filed: Jan. 29, 2019

Related U.S. Application Data

(60) Provisional application No. 62/624,120, filed on Jan. 31, 2018.

(51) Int. Cl.
| | | |
|---|---|---|
| *A61N 1/365* | (2006.01) | |
| *A61N 1/05* | (2006.01) | |
| *A61N 1/368* | (2006.01) | |
| *A61N 1/362* | (2006.01) | |
| *A61N 1/375* | (2006.01) | |
| *A61N 1/372* | (2006.01) | |
| *A61B 5/283* | (2021.01) | |

(52) U.S. Cl.
CPC ............ *A61N 1/057* (2013.01); *A61N 1/059* (2013.01); *A61N 1/3622* (2013.01); *A61N 1/3684* (2013.01); *A61N 1/3752* (2013.01); *A61N 1/37205* (2013.01); *A61N 1/37512* (2017.08); *A61B 5/283* (2021.01); *A61N 1/3756* (2013.01); *A61N 1/37288* (2013.01)

(58) Field of Classification Search
CPC .. A61N 1/057; A61N 1/3752; A61N 1/37205; A61N 1/3622; A61N 1/37512; A61N 1/059; A61N 1/3684; A61N 1/3756; A61N 1/37288
See application file for complete search history.

(56) References Cited

U.S. PATENT DOCUMENTS

| | | | |
|---|---|---|---|
| 2002/0193859 A1* | 12/2002 | Schulman | ............ A61N 1/3752 607/116 |
| 2006/0136004 A1 | 6/2006 | Cowan et al. | |
| 2007/0078490 A1 | 4/2007 | Cowan et al. | |
| (Continued) | | | |

FOREIGN PATENT DOCUMENTS

DE 202012006523 U1 9/2012

*Primary Examiner* — Eugene T Wu
(74) *Attorney, Agent, or Firm* — Nathan & Associates; Nathan Menachem (57) ABSTRACT

Pill-sized pacemaker system including a pill-size pacemaker and a lead connector, the pacemaker having a distal end including a first screw hook and a proximal end including a first magnetic coupler, the lead connector having a distal end including a second screw hook and a proximal end including a second magnetic coupler, the first and second magnetic couplers being disc-shaped, each including at least one depth-wise electrode, wherein the first screw hook is for screwing the pacemaker to inner heart tissue and for sensing at least one signal from the inner heart tissue, the second screw hook is for screwing the lead connector to inner heart tissue and for sensing at least one signal from the inner heart tissue, and the pacemaker and the lead connector are electrically coupled via each depth-wise electrode of the first and second magnetic couplers when the first and second magnetic couplers are magnetically coupled.

23 Claims, 6 Drawing Sheets

(56) References Cited

U.S. PATENT DOCUMENTS

| | | | |
|---|---|---|---|
| 2012/0109148 A1* | 5/2012 | Bonner | A61N 1/372 |
| | | | 606/129 |
| 2012/0109149 A1* | 5/2012 | Bonner | A61N 1/057 |
| | | | 606/129 |
| 2013/0110219 A1 | 5/2013 | Bomzin et al. | |
| 2013/0116740 A1* | 5/2013 | Bornzin | A61N 1/3756 |
| | | | 607/9 |
| 2013/0324825 A1 | 12/2013 | Ostroff et al. | |
| 2014/0172034 A1 | 6/2014 | Bomzin et al. | |
| 2015/0088155 A1* | 3/2015 | Stahmann | A61N 1/3756 |
| | | | 606/129 |
| 2015/0165199 A1 | 6/2015 | Karst et al. | |
| 2015/0196758 A1 | 7/2015 | Stahmann et al. | |
| 2015/0202431 A1 | 7/2015 | Bomzin et al. | |
| 2016/0008061 A1 | 1/2016 | Fung et al. | |
| 2016/0015287 A1* | 1/2016 | Anderson | A61N 1/3756 |
| | | | 600/510 |
| 2016/0067490 A1 | 3/2016 | Carney et al. | |
| 2017/0203104 A1* | 7/2017 | Nageri | A61B 5/6868 |
| 2019/0366081 A1* | 12/2019 | Kveen | A61N 1/0573 |

\* cited by examiner

PILL PACEMAKER WITH BI-V PACING, DDD PACING AND AAI WITH DDD BACKUP PACING

FIELD OF THE DISCLOSED TECHNIQUE

The disclosed technique relates to pill pacemakers, in general, and to methods and systems for increased pacing modes in pill pacemakers, in particular.

BACKGROUND OF THE DISCLOSED TECHNIQUE

Cardiac pacing in general refers to the medical intervention using electrical shocks applied to the heart to restore the heart's natural rhythm of pacing. Cardiac pacing is thus generally used to treat arrhythmias, which refer to a broad category of heart conditions wherein the heart either beats too slowly (such as bradycardia), too quickly (such as tachycardia) or irregularly (such as ventricular fibrillation). For a patient suffering from an arrhythmia, electrical shocks can be applied externally, for example using an automated external defibrillator (herein abbreviated AED) or internally if the patient has a device implanted in or around their heart which can apply an electrical shock. Such devices can be referred to as pacemakers, implantable cardioverter-defibrillators (herein abbreviated ICD), cardiac resynchronization therapy defibrillators (herein abbreviated CRT-D) and the like. These internally placed and implanted devices will herein be collectively referred to as heart devices. Such heart devices can be implanted subcutaneously (i.e., around the heart), epicardially (i.e., attached directly to the outer surface of the heart), intracardially (i.e., placed inside the heart) or intravascularly (i.e., placed in the veins and arteries surrounding the heart) or a combination of the above.

Besides their placement, such heart devices can also be classified according to various characteristics of how and where electrical shocks are delivered. For example, regarding pacemakers there is a standard nomenclature known as the NBG Pacemaker Code, a five position code of letters which describes various aspects of how and where electrical shocks are delivered by a pacemaker. The first position of the code describes what is paced by the pacemaker, with the options being V (for ventricle), A (for atrium), D (for dual, meaning both ventricle and atrium) and O (for none). The second position of the code describes which parts of the heart are sensed for signals that the pacemaker's processor may use to determine how and when electrical shocks (or in this context pacing signals) are to be applied. The options here again include V (for ventricle), A (for atrium), D (for dual, meaning both ventricle and atrium) and O (for none). In both the first and second positions, the code may include an indication if the left and/or right side of the heart is implied, for example, left ventricle sensing (such as LV), right ventricle pacing (such as RV), left atrium sensing (such as LA), right atrium pacing (such as RA), left and right ventricle sensing (LRV) or left and right atrium pacing (LRA). These codes are brought as mere examples. The third position of the code describes the response of the pacemaker to the sensed signals of the second position, with the options being T (for triggered, meaning a pacing signal is applied), I (for inhibited, meaning a pacing signal is held back or inhibited), D (for dual, meaning both triggered and inhibited) and O (for none). The fourth position of the code describes programmable options of the pacemaker, such as R (for rate modulated, meaning can the pacemaker vary the rate at which pacing signals are applied), C (for communicating, meaning can the pacemaker transmit and/or receive data for informational or programming purposes), M (for multiprogrammable, meaning the pacemaker can be programmed in more than three parameters), P (for simple programmable, meaning the pacemaker can be programmed in up to three parameters) and O (for none). The fifth position of the code describes if the pacemaker has any anti-tachycardiac functions, such as O (for none), P (for paced, meaning the pacemaker can attempt to pace a patient out of a tachycardia episode), S (for shocks, meaning the pacemaker can also shock the heart with higher voltage electrical shocks) and D (for dual, meaning paced and shocking). The fourth and fifth positions of the code are not always used to describe the functioning of pacemakers, however the first three positions are usually used. For example, a pacemaker listed as VVI would mean a pacemaker which can provide a pacing signal in the ventricle (the first 'V'), senses signals in the ventricle (the second 'V') and inhibits a pacing signal in the presence of a sensed event (the 'I'), whereas a pacemaker listed as VDD would mean a pacemaker which can provide a pacing signal in the ventricle (the 'V'), senses signals in the ventricle as well as the atrium (the first 'D') and can inhibit as well as trigger a pacing signal (the second 'D'). Other heart devices, such as ICDs, can also be described using the above code however other codes may be used to describe the functioning of ICDs and CRT-Ds in a similar manner.

A growing trend in the medical field, especially in the field of cardiology, is minimally invasive devices and procedures for treating arrhythmias. Such devices may be placed subcutaneously, epicardially, intracardiac or intravascularly and are usually considered minimally invasive in that open-heart surgery is not needed, with the device being placed and guided to its position in the body via a small incision providing access to the implantation site.

Figures 1A, 1B:
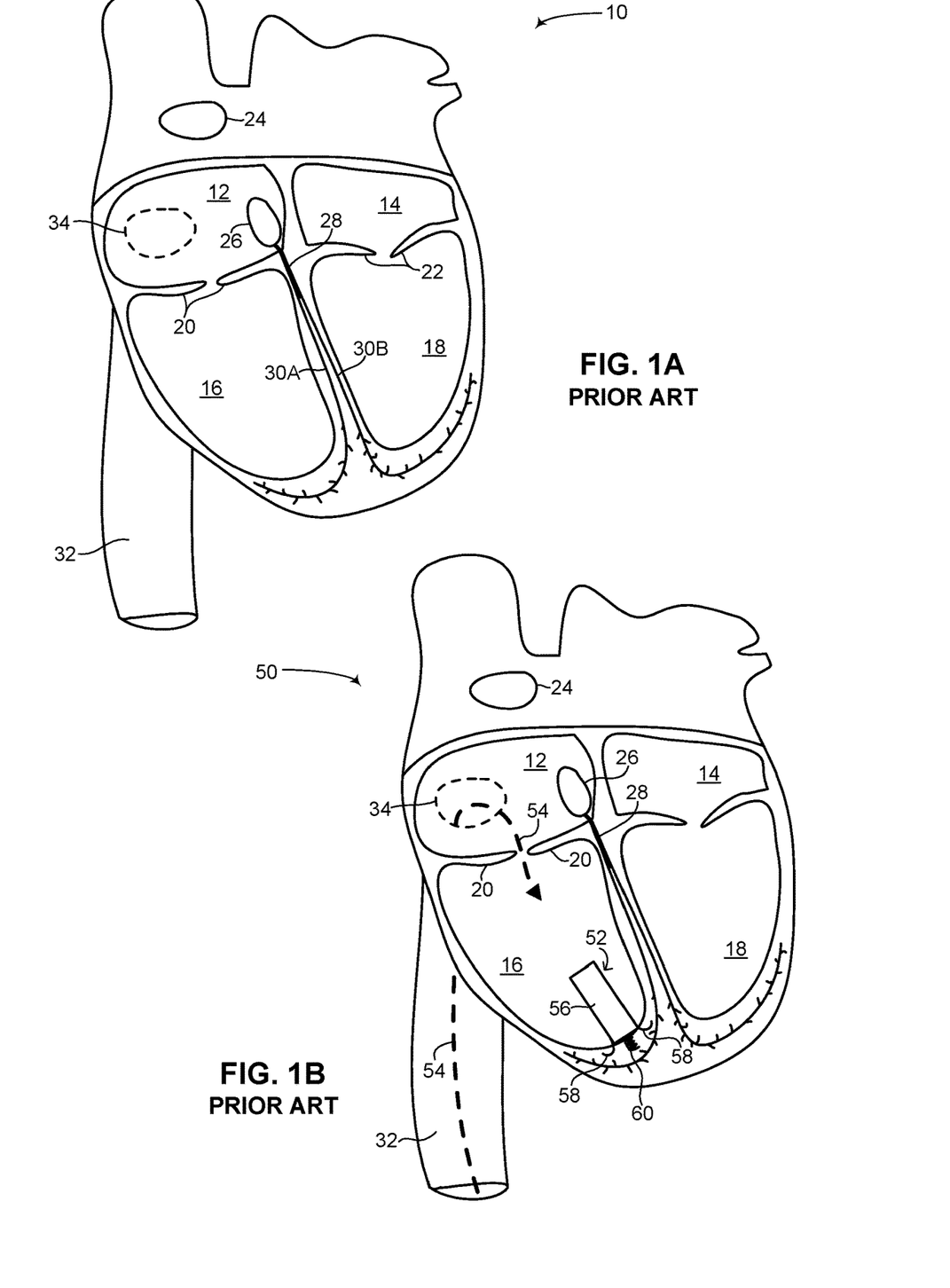
FIG. 1A is a schematic illustration of the heart of a human, as is known in the prior art.
FIG. 1B is a schematic illustration of the insertion of a pill pacemaker in the heart of a human, as is known in the prior art.

One such minimally invasive device is known as a pill pacemaker, which is placed in an intracardiac position, usually in the right ventricle. There is growing consensus in the field of cardiac pacing that pill pacemakers will revolutionize the treatment of arrhythmias considering their size (which is similar to a medical pill a person may swallow), their intracardiac placement (making them much less susceptible to myopotential noise) and their minimally invasive placement technique. Reference is now made to FIG. 1A, which is a schematic illustration of the heart of a human, generally referenced 10, as is known in the prior art. Heart 10 is shown in a cross-section view such that its major components are visible. Shown in FIG. 1A is a right atrium 12, a left atrium 14, a right ventricle 16 and a left ventricle 18. Shown as well are a tricuspid valve 20 and a mitral valve 22, a sinoatrial (herein abbreviated SA) node 24, an atrioventricular (herein abbreviated AV) node 26, a HIS bundle 28, a right bundle branch 30A and a left bundle branch 30B. Also shown is an inferior vena cava 32 and an opening 34 into which blood (not shown) in inferior vena cava 32 enters right atrium 12. Tricuspid valve 20 regulates the flow of blood from right atrium 12 into right ventricle 16 and mitral valve 22 regulates the flow of blood from left atrium 14 into left ventricle 18. SA node 24 is the natural pacemaker of heart 10 and provides an electric signal (not shown) which travels through the atria of the heart to AV node 26. The electric signal provided by SA node 24 triggers another electric signal in AV node 26 which travels down HIS bundle 28 and then along right and left bundle branches 30A and 30B, eventually reaching the Purkinje fibers (not labeled) which cause right ventricle 16 and left ventricle 18 to contract and pump blood out of the heart.

Reference is now made to FIG. 1B, which is a schematic illustration of the insertion of a pill pacemaker in the heart of a human, generally referenced 50, as is known in the prior art. Identical elements in FIGS. 1A and 1B are labeled using the same reference numbers. Shown in FIG. 1B is a pill pacemaker 52, which is known in the art, and can be, for example, the Micra™ from Medtronic® and the Nanostim™ leadless pacemaker from St. Jude Medical®. Pill pacemaker 52 includes a body 56, a plurality of hooks 58 and a screw hook 60. Plurality of hooks 58 and screw hook 60 are used to firmly attached pill pacemaker 52 to the lower end of right ventricle 16. Body 56 includes a power source (not shown) and electronics (not shown) for sensing signals and applying a pacing signal to right ventricle 16. Signals by pill pacemaker 52 are both sensed and applied via screw hook 60 which is made from a conductive metal.

Pill pacemaker 52 is inserted into the heart via a known minimally invasive procedure wherein an incision is made in the right femoral vein (not shown) which leads up to and couples with inferior vena cava 32. A guidewire (not shown) is guided from the incision, up the right femoral vein, through inferior vena cava 32 into the heart via opening 34 into right atrium 12. Using known imaging technologies (such as real-time X-ray), the guidewire is guided from right atrium 12 via tricuspid valve 20 into right ventricle 16 to the lower end of the right ventricle. This is shown schematically in FIG. 1B via an arrow 54. A catheter (not shown) attached to pill pacemaker 52 can then be inserted over the guidewire, carrying pill pacemaker 52 to its desired position inside right ventricle 16. Once properly positioned, the catheter can be turned to twist screw hook 60 into place and to attach plurality of hooks 58 to the inner wall (not labeled) of right ventricle 16. Plurality of hooks 58 and screw hook 60 are sufficiently strong when properly attached to the inner wall of right ventricle 16 to remain coupled with the inner wall of the right ventricle as blood is constantly moved in and out of right ventricle 16.

Pill pacemaker 52 is limited in that in can only operate in a VVI mode, providing pacing signals in the right ventricle (the first 'V'), sensing signals in the right ventricle (the second 'V') and inhibiting a pacing signal in the presence of a sensed event (the T). Whereas VVI pacing is helpful in many patients suffering from arrhythmias, most patients receiving pacemakers require heart devices that can operate in other modes besides VVI. Most patients therefore receive intravascular or intracardial pacemakers which can operate in both ventricles (known as biventricular (herein abbreviated Bi-V) pacing and usually effected by a CRT-D), in a DDD mode or in an AAI mode with DDD backup pacing. For example, a patient suffering from atrial fibrillation with slow ventricular rates will often require a Bi-V pacemaker to prevent iatrogenic univentricular pacing induced dyssynchrony which can worsen or even cause a cardiomyopathy. Pill pacemakers cannot operate in these modes as they can only sense and deliver pacing signals in a single ventricle, usually the right ventricle.

Pill pacemakers, also known as leadless pacemakers, are known in the art. For example US patent application publication no. 2006/0136004 to Cowan et al., assigned to EBR Systems, Inc., entitled "Leadless tissue stimulation systems and methods" is directed to a system including an implantable receiver-stimulator and an implantable controller-transmitter which are used for leadless electrical stimulation of body tissues. Cardiac pacing and arrhythmia control is accomplished with one or more components including implantable receiver-stimulators and an external or implantable controller-transmitter. The components are implanted by testing external or implantable devices at different tissue sites, observing physiologic and device responses, and selecting sites with preferred performance for implanting the components. In this system, a controller-transmitter is activated at a remote tissue location to transmit/deliver acoustic energy through the body to a receiver-stimulator at a target tissue location. The receiver-stimulator converts the acoustic energy to electrical energy for electrical stimulation of the body tissue. The tissue locations can be optimized by moving either or both of the controller-transmitter and the receiver-stimulator to determine the best patient and device responses.

US patent application publication no. 2016/0067490 to Carney et al., assigned to Medtronic, Inc., entitled "Dual Chamber Timing for Leadless Pacemakers Using Infrequent Atrial Signals and Ventricular Contractions" is directed to a method for adjusting a pacing rate in a dual-chamber, leadless pacemaker implanted in a heart. The method involves a leadless atrial pacemaker implanted in an atrium of the heart and a leadless ventricular pacemaker implanted in a ventricle of the heart. According to the method, the leadless atrial pacemaker determines that an intrinsic atrial contraction rate of the atrium is faster than a ventricular contraction rate. The atrial pacemaker transmits a first signal to the ventricular pacemaker to increase a ventricular pacing rate of the ventricular pacemaker. The ventricular pacemaker receives the transmitted first signal and increases the ventricular pacing rate, based on the received first signal.

US patent application publication no. 2013/0110219 to Bornzin et al., assigned to Pacesetter, Inc., entitled "Unitary Dual-Chamber Leadless Intra-Cardiac Medical Device and Method of Implanting Same" is directed to an assembly for introducing a leadless intra-cardiac medical device including a sheath having an internal passage, wherein the sheath is configured to be maneuvered into the heart of the patient. A housing may be retained within the internal passage, wherein the housing is configured to be pushed out of the sheath, the housing having a first anchoring member configured to anchor the housing to a first implant location within the heart. The assembly includes an electrode trailing the housing within the internal passage, wherein the electrode is also configured to be pushed out of the sheath. The electrode has a second anchoring member configured to anchor the electrode to a second implant location within the heart. A conductive wire connects the housing to the electrode, wherein movement of the housing out of the sheath causes the electrode to follow the movement to a distal end of the sheath.

Other prior art relating to leadless pacemakers includes US patent application publication nos. US 2007/0078490, 2013/0116740, 2013/0324825, 2014/0172034, 2015/0165199, 2015/0196758 and 2015/0202431.

SUMMARY OF THE DISCLOSED TECHNIQUE

It is an object of the disclosed technique to provide a novel method and system for a pill-sized pacemaker system including a pill pacemaker and a separate lead connector having a magnetic coupler. In accordance with the disclosed technique, there is thus provided a pill-sized pacemaker system including a pill-sized pacemaker and a lead connector. The pill-sized pacemaker has a distal end which includes a first screw hook and a proximal end which includes a first magnetic coupler. The lead connector has a distal end which includes a second screw hook and a proximal end which includes a second magnetic coupler. The first magnetic coupler and the second magnetic coupler are disc-shaped and include at least one respective depth-wise electrode. The first screw hook is for screwing the pill-size pacemaker to a first inner heart tissue and for sensing at least one signal from the first inner heart tissue. The second screw hook is for screwing the lead connector to a second inner heart tissue and for sensing at least one signal from the second inner heart tissue. The pill-sized pacemaker and the lead connector are electrically coupled via each one of the respective depth-wise electrode of the first magnetic coupler and the second magnetic coupler when the first magnetic coupler and the second magnetic coupler are magnetically coupled.

In accordance with another aspect of the disclosed technique, there is thus provided a pill-sized pacemaker system including a pill-sized pacemaker and a lead connector. The pill-sized pacemaker has a distal end which includes a first screw hook and a proximal end which includes a first magnetic coupler and a male coupling extension. The lead connector has a distal end which includes a second screw hook and a proximal end which includes a second magnetic coupler and a female coupling extension. The male coupling extension includes at least one electrical connector and the female coupling extension includes at least one respective electrical connector. The first magnetic coupler and the second magnetic coupler are disc-shaped. The first screw hook is for screwing the pill-size pacemaker to a first inner heart tissue and for sensing at least one signal from the first inner heart tissue. The second screw hook is for screwing the lead connector to a second inner heart tissue and for sensing at least one signal from the second inner heart tissue. The pill-sized pacemaker and the lead connector are electrically coupled via the electrical connector of the male coupling extension and the respective electrical connector of the female coupling extension when the female coupling extension is positioned over the male coupling extension and the first magnetic coupler is magnetically coupled with the second magnetic coupler.

In accordance with a further aspect of the disclosed technique, there is thus provided a pill-sized pacemaker system including a pill-sized pacemaker and a multiple lead connector. The pill-sized pacemaker has a distal end which includes a first screw hook and a proximal end which includes a first magnetic coupler and a male coupling extension. The multiple lead connector has at least two distal ends and a proximal end. Each distal end includes a respective screw hook and the proximal end includes a second magnetic coupler and a female coupling extension. The male coupling extension includes at least two electrical connectors and the female coupling extension includes at least two respective electrical connectors. The first and second magnetic couplers are disc-shaped. The first screw hook is for screwing the pill-size pacemaker to a first inner heart tissue and for sensing at least one signal from the first inner heart tissue. Each respective screw hook of the multiple lead connector is for screwing each distal end to a respective at least second inner heart tissue and third inner heart tissue and for sensing at least one signal from the second and third inner heart tissues. The pill-sized pacemaker and the multiple lead connector are electrically coupled via the electrical connectors of the male coupling extension and the respective electrical connectors of the female coupling extension when the female coupling extension is positioned over the male coupling extension and the first magnetic coupler is magnetically coupled with the second magnetic coupler.

In accordance with another aspect of the disclosed technique, there is thus provided a method for placement of a pill-sized pacemaker system in the heart of a patient. The pill-sized pacemaker system includes a pill-sized pacemaker, a lead connector, a first insertion tool and a second insertion tool. The pill-sized pacemaker has a first distal end which includes a first screw hook and a first proximal end which includes a first magnetic coupler. The lead connector has at least one second distal end which includes a respective second screw hook and a second proximal end which includes a second magnetic coupler. The pill-sized pacemaker and the lead connector are electrically coupled when the first magnetic coupler and the second magnetic coupler are magnetically coupled. The method includes the procedures of making an incision in a right femoral vein of the patient, guiding a guidewire from the incision to a first desired position in the heart and coupling the pill-sized pacemaker to the first insertion tool. The method also includes the procedures of guiding the first insertion tool over the guidewire to the first desired position, turning the first insertion tool to twist the first screw hook into the first desired position and removing the first insertion tool. The method further includes the procedures of guiding the guidewire to a second desired position in the heart, coupling the lead connector to the first insertion tool and guiding the first insertion tool over the guidewire to the second desired position. The method then includes the procedures of turning the first insertion tool to twist the respective second screw hook into the second desired position, removing the first insertion tool and guiding the second insertion tool over the guidewire to the second desired position and grabbing the second magnetic coupler. The method further includes the procedures of guiding the second magnetic coupler to the first desired position, turning the second insertion tool to align the second magnetic coupler with the first magnetic coupler and moving the second magnetic coupler in close proximity to the first magnetic coupler using the second insertion tool such that the second magnetic coupler is magnetically coupled with the first magnetic coupler. The method finally includes the procedures of removing the second insertion tool, removing the guidewire and suturing up the incision.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a novel pill-sized pacemaker system including a pill pacemaker and a separate lead connector having a magnetic coupler. The pill pacemaker is positioned in a ventricle of a patient, usually the right ventricle, and the lead connector can be coupled with any one of the SA node, the AV node, the HIS bundle, the other ventricle of the heart, the coronary sinus (to pace the left ventricle) or either one of the atria of the heart. The pill pacemaker and the lead connector each include a magnet. Once the pill pacemaker is positioned in the heart of the patient and the lead connector is also positioned in the heart of the patient, the two components are electrically coupled via the magnetic coupler thus enabling the pill pacemaker to sense signals from other parts of the heart and to deliver electric shocks to those other parts of the heart. According to the disclosed technique, the benefits of a pill pacemaker given its size, its intracardiac placement (thereby making it much less susceptible to myopotential noise) and its minimally invasive placement technique are possible while also enabling a pill-sized pacemaker to function in other modes besides a VVI mode, such as a DDD mode, an AAI mode with DDD backup pacing and also with the possibility of providing Bi-V pacing.

Figure 2A:
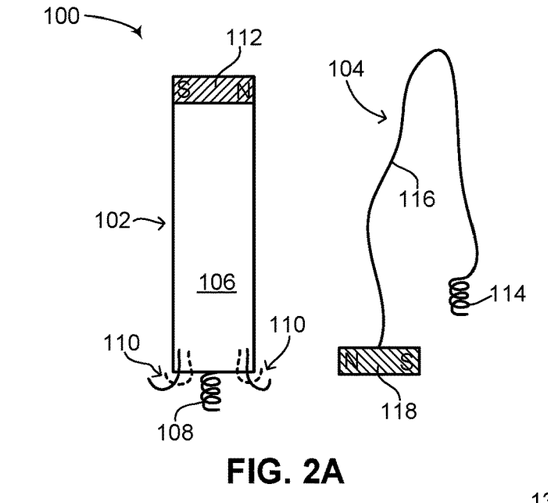
FIG. 2A is a schematic illustration of a pill-sized pacemaker system, constructed and operative in accordance with an embodiment of the disclosed technique.

Reference is now made to FIG. 2A which is a schematic illustration of a pill-sized pacemaker system, generally referenced 100, constructed and operative in accordance with an embodiment of the disclosed technique. Pill-sized pacemaker system 100 includes a pill-sized pacemaker 102 and a lead connector 104. Pill-sized pacemaker 102 includes a body 106, a screw hook 108, a plurality of hooks 110 and a first strong magnet 112. Lead connector 104 includes a screw hook 114, a lead wire 116 and a second strong magnet 118. Body 106 can be cylindrical in shape and houses electronics (not shown) as well as a power supply (not shown) for enabling the functioning of pill-sized pacemaker 102. Body 106 may also optionally include at least one capacitor for providing high voltage electric shocks (such as in the case of a pacemaker having defibrillation functions). Body 106 can further include a receiver-transmitter (not shown) for receiving and transmitting signals wirelessly. The power supply provides power to operate the electronics and to provide power for electric shocks to the heart. The electronics monitor signals in the heart of a patient (not shown) and can determine if and when an electric shock should be provided to the heart or not. The electronics enable pill-sized pacemaker 102 to operate in various pacing modes, such as VVI, DDD, AAI and the like.

Screw hook 108 is made from a biocompatible metal and is used to screw pill-sized pacemaker 102 to the inner tissue of the heart of the patient, such as the right ventricle or the left ventricle from inside the heart. Screw hook 108 is also used to sense signals from the ventricle it is screwed into and to provide electric shocks as well. Plurality of hooks 110 provide further support for coupling body 106 with the inner tissue of the heart and to prevent body 106 from disengaging from its screwed in position, especially considering the constant flow of blood in and out of the ventricles. First strong magnet 112 can be a neodymium magnet or any other strong permanent magnet which is biocompatible. As shown, first strong magnet 112 includes a north end and a south end. Screw hook 114 is similar to screw hook 108, is also made from a biocompatible metal, and is used to screw lead connector 104 to the inner tissue of the heart, such as a ventricle, an atrium, the tissue of the SA node, the tissue of the AV node, the tissue of the HIS bundle or the tissue of the coronary sinus. Screw hook 114 is also used to sense signals from the tissue it is screwed into and to provide electric shocks as well. Lead wire 116 is an electrical lead and is used to transmit signals to and from screw hook 114. Second strong magnet 118 is similar to first strong magnet 112 and can also be a neodymium magnet or any other strong permanent magnet which is biocompatible. Shown as well is the north end and south end of second strong magnet 118. It is noted that body 106 may have a cylindrical shape and thus first strong magnet 112 is shaped like a thin disc. Second strong magnet 118 has a shape similar to first strong magnet 112 and thus may also be shaped like a thin disc.

First strong magnet 112 and second strong magnet 118 can be coupled together as magnets via the magnetic force, thus coupling pill-sized pacemaker 102 with lead connector 104. Considering that magnets in general are not good conductors, each of first strong magnet 112 and second strong magnet 118 may include electrodes (not shown) for increasing the conductance of energy between the two magnets. This is shown in greater detail below in FIGS. 2B, 5 and 6. Once the two magnets are coupled, body 106 can receive sensed signals from both of screw hooks 108 and 114, thus increasing the sensing capabilities of pill-sized pacemaker 102 to at least two different parts of the heart. In addition, body 106 can also provide electric shocks via either one of or both of screw hooks 108 and 114, thereby also increasing the therapy capabilities of pill-sized pacemaker 102.

Figure 2B:
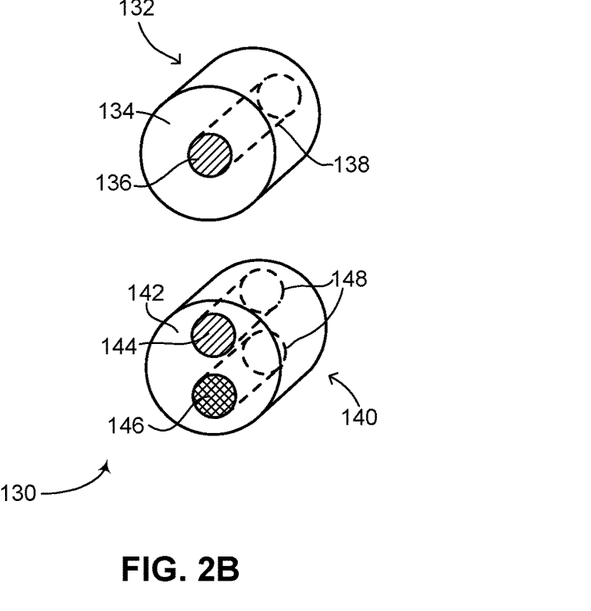
FIG. 2B is a schematic perspective illustration of the magnetic disc of the pill-sized pacemaker system of FIG. 2A, constructed and operative in accordance with another embodiment of the disclosed technique.

Reference is now made to FIG. 2B which is a schematic perspective illustration of the magnetic disc of the pill-sized pacemaker system of FIG. 2A, generally referenced 130, constructed and operative in accordance with another embodiment of the disclosed technique. FIG. 2B shows two different embodiments of the magnetic disc used with the pill-sized pacemaker and the lead connector of the disclosed technique. A first embodiment 132 is shown with one electrode whereas a second embodiment 140 is shown with two electrodes. Magnetic disc 130 can be used to embody either one of first strong magnet 112 (FIG. 2A) and second strong magnet 118 (FIG. 2A) or both. First embodiment 132 shows the magnet having a strong permanent magnetic disc 134 and a single electrode 136 running along the depth of the magnet, as shown by dotted lines 138. Thus electrode 136 extends the length of magnetic disc 134 and enables a good electrical connection via the magnet. First embodiment 132 can be used in embodiments of the disclosed technique where unipolar pacing is required. Second embodiment 140 shows the magnet having a strong permanent magnetic disc 142 and two electrodes 144 and 146 running along the depth of the magnet, as shown by dotted lines 148. Thus electrodes 144 and 146 extend the length of magnetic disc 142 and enable a good electrical connection via the magnet. Second embodiment 140 can be used in embodiments of the disclosed technique where bipolar pacing is required. When two of the magnet embodiments shown in FIG. 2B are positioned together such that their magnetic poles attract, a solid and good electrical connection is made between single electrode 136 or between electrodes 144 and 146. Lead wire 116 (FIG. 2A) may be coupled to one end of electrode 136 or electrodes 144 and 146 of one of the strong magnets and an electrical connection (not shown) on body 106 (FIG. 2A) may be coupled with one end of electrode 136 or electrodes 144 and 146 of the other one of the strong magnets. Thus when the magnets are coupled together by the magnetic force a good electrical connection is made.

Figure 3A:
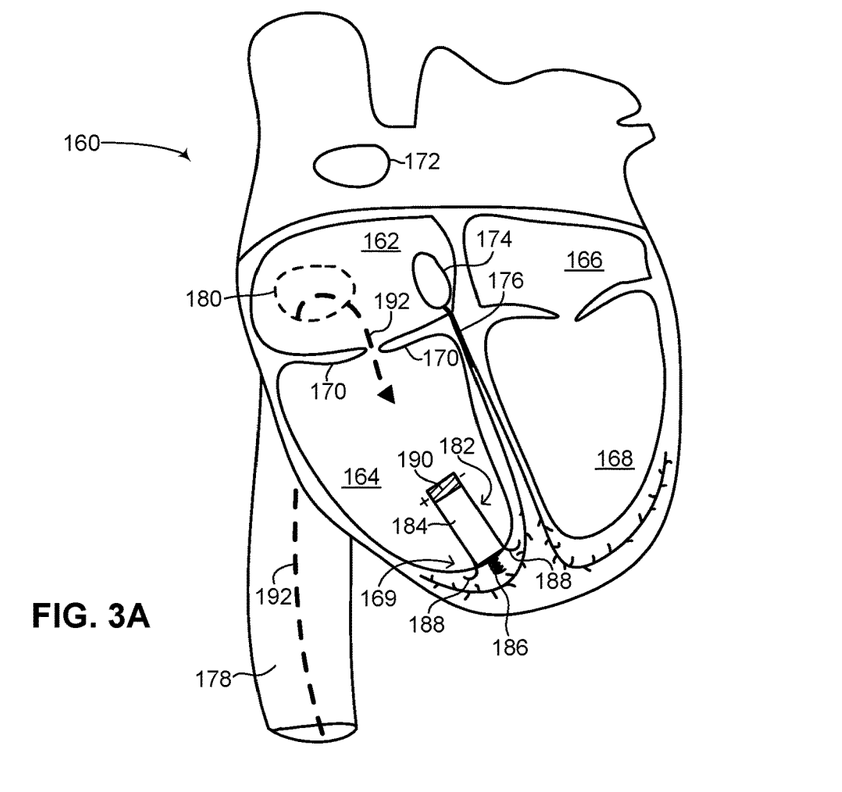
FIGS. 3A-3D are schematic illustrations of the placement of the pill-sized pacemaker system of FIG. 2A in the heart of a patient in a first embodiment, constructed and operative in accordance with a further embodiment of the disclosed technique.

Reference is now made to FIGS. 3A-3D which are schematic illustrations of the placement of the pill-sized pacemaker system of FIG. 2A in the heart of a patient in a first embodiment, generally referenced 160, 200, 220 and 240 respectively, constructed and operative in accordance with a further embodiment of the disclosed technique. Identical elements in FIGS. 3A-3D are labeled using the same reference numbers for the purposes of simplicity. With reference to FIG. 3A, shown is a heart of a patient, including a right atrium 162, a right ventricle 164, a left atrium 166 and a left ventricle 168. Shown as well is a tricuspid valve 170, an SA node 172, an AV node 174 and a HIS bundle 176. Also shown is an inferior vena cava 178 and its opening 180 into right atrium 162.

The pill-sized pacemaker of the disclosed technique is inserted into the right ventricle of a patient using known techniques as described in the prior art. As shown is a pill-sized pacemaker 182 of the disclosed technique, including a body 184, a screw hook 186, a plurality of hooks 188 and a first strong magnet 190. Pill-sized pacemaker 182 is substantially similar to pill-sized pacemaker 102 (FIG. 2A) and will not be described further. Pill-sized pacemaker 182 is inserted into right ventricle 164 via a path 192, which has an entry point into the patient via the right femoral vein (not shown). Prior to what is shown in FIG. 3A, according to the disclosed technique, an incision is made in the right femoral vein and a guidewire (not shown) is inserted and guided up the right femoral vein into inferior vena cava 178 and through opening 180 into right atrium 162. Using known imaging technologies, such as real-time X-ray, ultrasound, fluoroscopy and the like, the guidewire is guided through tricuspid valve 170 into right ventricle 164 and further into a lower end (or apex) 169 of right ventricle 164. Pill-sized pacemaker 182 is coupled with a guiding catheter or insertion tool (not shown) and inserted over the guidewire and guided into apex 169 of right ventricle 164. Using screw hook 186 and plurality of hooks 188, pill-sized pacemaker 182 is coupled with lower end 169 of right ventricle 164 by screwing it into the tissue on the inner side of right ventricle 164. In the case of a patient requiring only a VVI pacing mode, the pill-sized pacemaker of the disclosed technique can be used as is without the lead connector (as shown in FIG. 2A). The insertion tool can then be removed from the patient while leaving the guidewire.

Figures 3B, 3C:
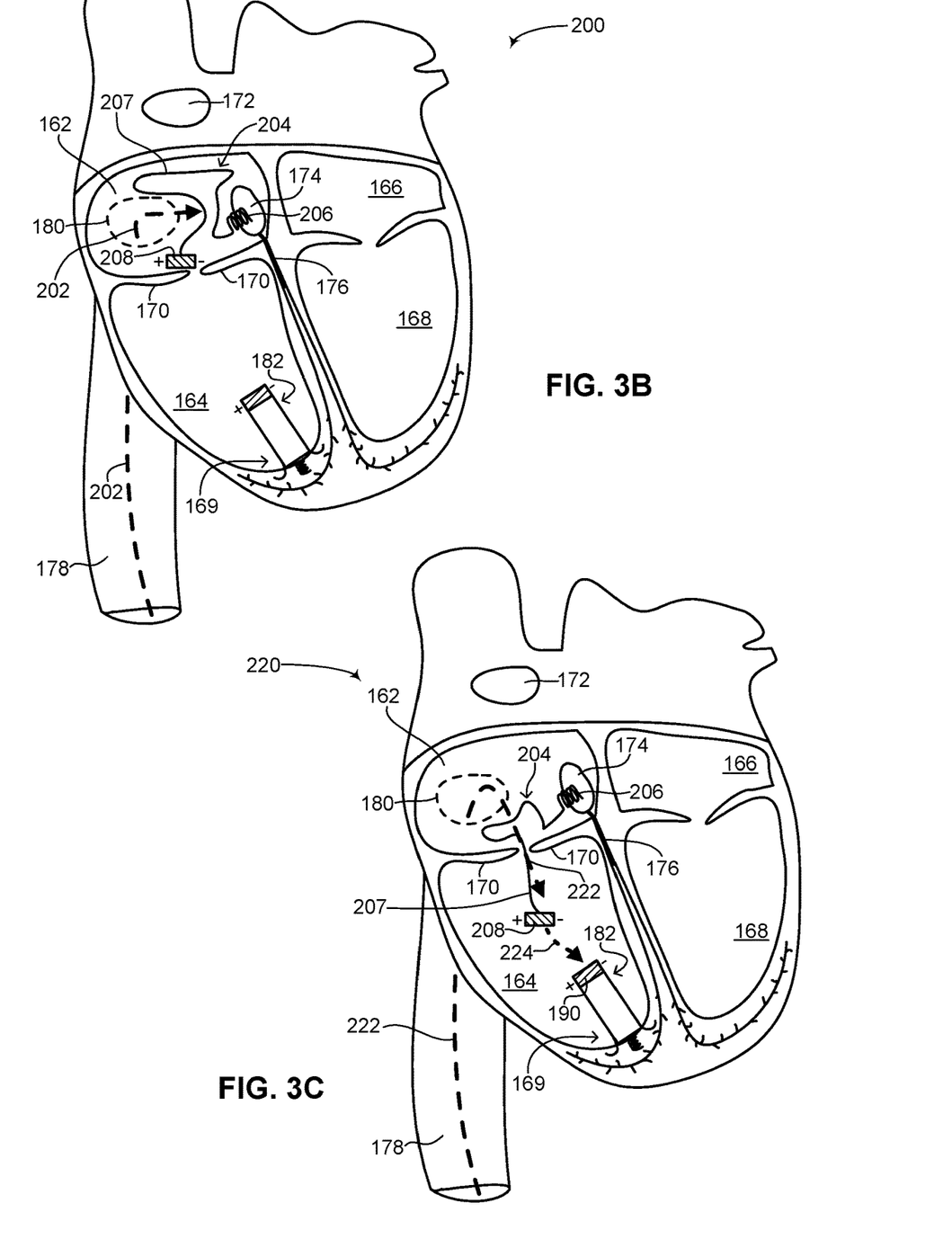

With reference to FIG. 3B, the guidewire is removed from right ventricle 164 and guided to AV node 174 as shown by a path 202. Shown in FIG. 3B is a lead connector 204, which is substantially similar to lead connector 104 (FIG. 2A). Lead connector 204 includes a screw hook 206, a lead wire 207 and a second strong magnet 208. Lead connector 204 is coupled with the insertion tool and guided over the guidewire into right ventricle 162 towards AV node 174. Using the insertion tool, screw hook 206 is screwed into AV node 174 and all of lead wire 207 and second strong magnet 208 is inserted into right atrium 162 and allowed to float free in the right atrium. The location of AV node 174 can be determined using known imaging technology. It is noted that in FIG. 2B, screw hook 206 is screwed into AV node 174 however in another embodiment screw hook 206 can be screwed into HIS bundle 176 or into the coronary sinus (not shown). The particular placement of screw hook 206 in right atrium 162 depends on the arrhythmia of the patient which is being treated by pacing therapy and the pacing mode or modes required for the therapy. For example, if peri-Hisian pacing is required, then screw hook 206 should be coupled with HIS bundle 176. If a DDD pacing mode is required, then screw hook 206 should be coupled with SA node 172 (shown below in FIG. 4). If biventricular pacing is needed, then screw hook could be inserted into the coronary sinus to pace the left ventricle. The insertion tool used to insert lead connector 204 is then removed while leaving the guidewire in right atrium 162. It is noted that the same insertion tool can be used to insert and screw pill-sized pacemaker 182 into apex 169 of right ventricle 164 and to insert and screw lead connector 204 into AV node 174 in right atrium 162.

With reference to FIG. 3C, a second insertion tool (not shown) is guided over the guidewire into right atrium 162 and is used to grab second strong magnet 208. Again using known imaging technologies, the position of second strong magnet 208 can be determined in right atrium 162 and attached to the second insertion tool. The second insertion tool is then used to guide second strong magnet 208 through tricuspid valve 170 into right ventricle 164, shown by a path 222. Once inside right ventricle 164, the second insertion tool is used to align second strong magnet 208 with first strong magnet 190, shown by a path 224. The second insertion tool is then used to bring second strong magnet 208 in close proximity to first strong magnet 190 such that the two magnets are attracted via the magnetic force. The second insertion tool is then removed, as is the guidewire, and the incision in the patient is sutured up.

Figures 3D, 4:
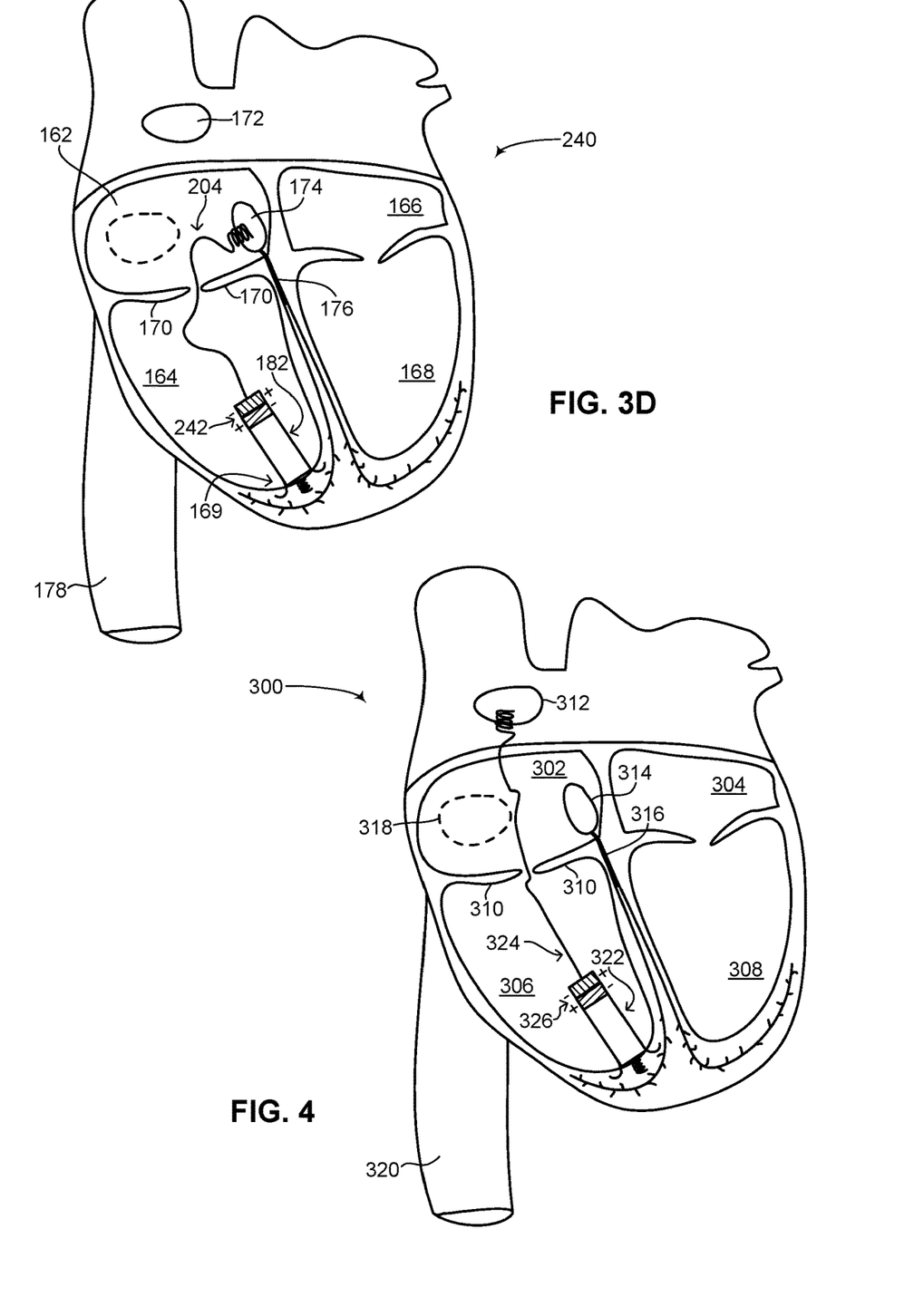
FIG. 4 is a schematic illustration of the placement of the pill-sized pacemaker system of FIG. 2A in the heart of a patient in a second embodiment, constructed and operative in accordance with another embodiment of the disclosed technique.

With reference to FIG. 3D, the pill-sized pacemaker system of the disclosed technique is shown fully and properly positioned in the heart of a patient, with pill-sized pacemaker 182 screwed into apex 169 of right ventricle 164 and lead connector 204 screwed into AV node 174. Shown as well is the coupling between pill-sized pacemaker 182 and lead connector 204 via an arrow 242, with both strong magnets attached via the magnetic force. As described above, each strong magnet includes an electrode such that good electrical conduction is made between pill-sized pacemaker 182 and lead connector 204. The electronics (not shown) of pill-sized pacemaker 182 now have access to sensed signals from right atrium 162 and can also provide electric shocks to AV node 174 (or as shown below in FIG. 4 to SA node 172). Thus according to the disclosed technique, the pill-sized pacemaker system enables a pill-sized pacemaker to function in an AAI mode or a DDD mode, sensing and also providing electric shocks to both the right ventricle and the right atrium. As mentioned above, the screw hook of lead connector 204 can also be coupled with HIS bundle 176. In such an embodiment, the pill-sized pacemaker system of the disclosed technique enables the pill-sized pacemaker to function as a peri-Hisian pacemaker with backup VVI pacing. It is noted that in such an embodiment, lead connector 204 can sense activity in right atrium 162 and enable pill-sized pacemaker 182 to function in a VDD mode, enabling atrial sensing (the second 'ID') along with peri-Hisian pacing (since lead connector 204 is screwed into HIS bundle 176) in the case of an occurrence of heart block.

Reference is now made to FIG. 4 which is a schematic illustration of the placement of the pill-sized pacemaker system of FIG. 2A in the heart of a patient in a second embodiment, generally referenced 300, constructed and operative in accordance with another embodiment of the disclosed technique. Shown is a heart of a patient, including a right atrium 302, a right ventricle 304, a left atrium 306 and a left ventricle 308. Shown as well is a tricuspid valve 310, an SA node 312, an AV node 314 and a HIS bundle 316. Also shown is an inferior vena cava 320 and its opening 318 into right atrium 302. Using a similar procedure as shown above in FIGS. 3A-3D, a pill-sized pacemaker system of the disclosed technique, including a pill-sized pacemaker 322 and a lead connector 324, can be inserted and attached to both the apex of right ventricle 304 and SA node 312. Shown via an arrow 326 is the magnetic coupling between pill-sized pacemaker 322 and lead connector 324. The placement of the pill-sized pacemaker system as shown in FIG. 4 can be used to operate pill-sized pacemaker 322 in a DDD, AAI, VVI, VDD and ADD pacing mode. In addition to the aforementioned pacing modes, pill-sized pacemaker 322 can include a rate sensor (not shown) thus allowing rate responsive pacing for all the aforementioned pacing modes. These therapies can be used for treating complete heart block, high-grade AV block, symptomatic AV block and SA node dysfunction. In the case where the lead connector is placed in the distal coronary sinus (not shown) biventricular pacing can be achieved allowing for cardiac re-synchronization pacing and treatment of congestive heart failure due to cardiac desynchrony.

Figure 5:
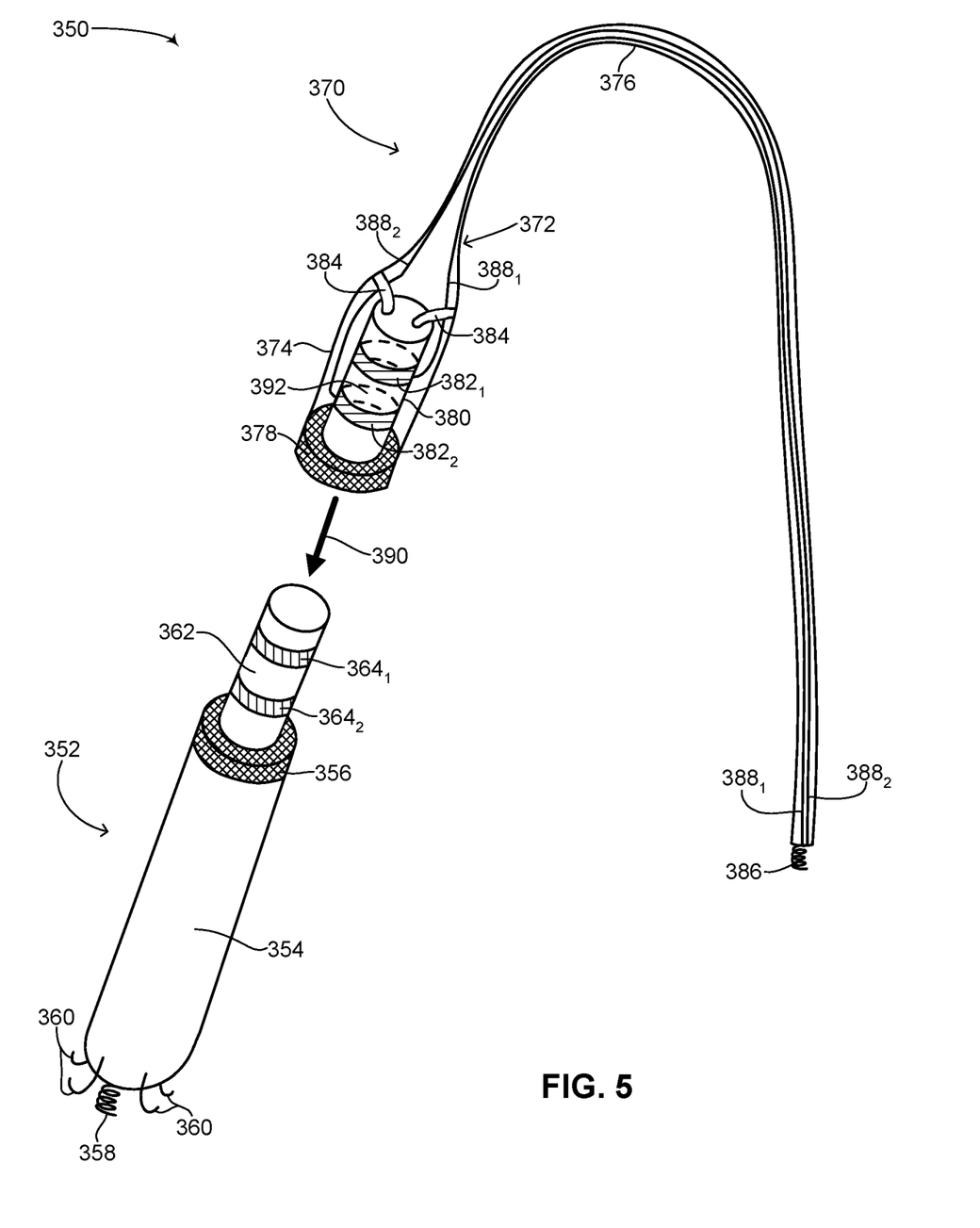
FIG. 5 is a schematic illustration of a single lead pill-sized pacemaker system, constructed and operative in accordance with a further embodiment of the disclosed technique.

Reference is now made to FIG. 5 which is a schematic illustration of a single lead pill-sized pacemaker system, generally referenced 350, constructed and operative in accordance with a further embodiment of the disclosed technique. Single lead pill-sized pacemaker system 350 includes a pill-sized pacemaker 352 and a lead connector 370. Pill-sized pacemaker 352 includes a body 354, a magnetic disc 356, a screw hook 358, a plurality of hooks 360 and a male coupling extension 362. Body 354, magnetic disc 356, screw hook 358 and plurality of hooks 360 are respectively substantially similar to body 106 (FIG. 2A), screw hook 108 (FIG. 2A), plurality of hooks 110 (FIG. 2A) and first strong magnet 112 (FIG. 2A). Magnetic disc 356 has a hole (not shown) via which male coupling extension 362 is firmly coupled with body 354. Male coupling extension 362 includes two electrical connectors $364_1$ and $364_2$, which are electrically coupled with the electronics (not shown) in body 354.

Lead connector 370 includes a connector end 374 and a lead 376. Connector end 374 includes a magnetic disc 378, a female coupling extension 380, two electrical connectors $382_1$ and $382_2$ and a plurality of drainage channels 384. The end of lead 376 includes a screw hook 386. A first wire $388_1$ electrically couples electrical connector $382_1$ with screw hook 386 whereas a second wire $388_2$ electrically couples electrical connector $382_2$ with screw hook 386. Female coupling extension 380 is hollow, as shown by a line 392, such that it can be placed over male coupling extension 362, as shown by an arrow 390. Lead connector 370 narrows at the distal end of female coupling extension 380, as shown by an arrow 372. Pill-sized pacemaker system 350 is shown having two electrical connectors, which can be used in bipolar pacing. However it is noted that pill-sized pacemaker system 350 can also include only a single electrical connector in the male and female coupling extensions (not shown) for unipolar pacing.

Each one of magnetic discs 356 and 378 can be a neodymium magnet or other type of strong permanent magnet which is biocompatible. Once female coupling extension 380 is positioned over male coupling extension 362, magnetic discs 356 and 378 are coupled together via the magnetic force thereby firmly coupling pill-sized pacemaker 352 with lead connector 370. Electrical connectors $364_1$ and $364_2$ are aligned such that they make electrical contact with electrical connectors $382_1$ and $382_2$ when female coupling extension 380 is positioned over male coupling extension 362. Plurality of drainage channels 384 enable any blood present in female coupling extension 380 to escape when female coupling extension 380 is positioned over male coupling extension 362. Once pill-sized pacemaker 352 and lead connector 370 are coupled together, the electronics (not shown) in body 354 are electrically coupled with screw hook 386 as well as screw hook 358, enabling signals to be sensed and electric shocks to be delivered via either one of screw hooks 386 or 358, or via both. Pill-sized pacemaker system 350 is substantially similar to pill-sized pacemaker system 100 (FIG. 2A), however the coupling mechanism between the pill-sized pacemaker and the lead connector is slightly different. As explained above, screw hook 358 is positioned in the right ventricle of the heart whereas screw hook 386 can be positioned in the right atrium, attached to the HIS bundle, the SA node, the AV node or even the coronary sinus.

Figure 6:
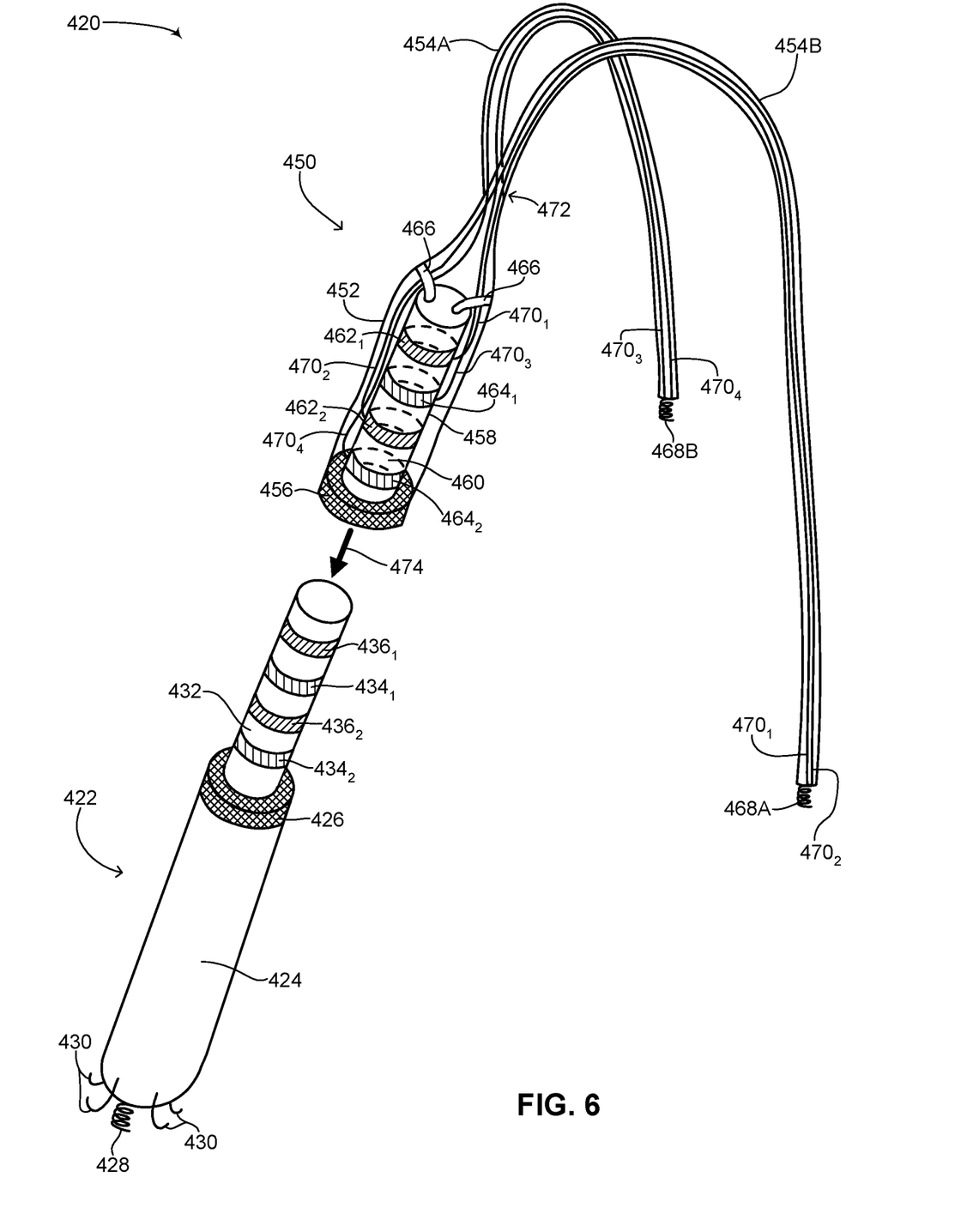
FIG. 6 is a schematic illustration of a double lead pill-sized pacemaker system, constructed and operative in accordance with another embodiment of the disclosed technique.

Reference is now made to FIG. 6 which is a schematic illustration of a double lead pill-sized pacemaker system, generally referenced 420, constructed and operative in accordance with another embodiment of the disclosed technique. Double lead pill-sized pacemaker system 420 includes a pill-sized pacemaker 422 and a double lead connector 450. Pill-sized pacemaker 422 includes a body 424, a magnetic disc 426, a screw hook 428, a plurality of hooks 430 and a male coupling extension 432. Body 424, magnetic disc 426, screw hook 428 and plurality of hooks 430 are respectively substantially similar to body 106 (FIG. 2A), screw hook 108 (FIG. 2A), plurality of hooks 110 (FIG. 2A) and first strong magnet 112 (FIG. 2A). Magnetic disc 426 has a hole (not shown) via which male coupling extension 432 is firmly coupled with body 424. Male coupling extension 432 includes two sets of electrical connectors, a first set of electrical connectors $434_1$ and $434_2$ and a second set of electrical connectors $436_1$ and $436_2$, which are electrically coupled with the electronics (not shown) in body 424.

Double lead connector 450 includes a connector end 452, a first lead 454A and a second lead 454B. Connector end 452 includes a magnetic disc 456, a female coupling extension 458, two sets of electrical connectors, a first set of electrical connectors $462_1$ and $462_2$ and a second set of electrical connectors $464_1$ and $464_2$ and a plurality of drainage channels 466. The end of each one of first lead 454A and second lead 454B includes a respective screw hook 468A and 468B. A first wire $470_1$ electrically couples electrical connector $462_1$ with screw hook 468A whereas a second wire $470_2$ electrically couples electrical connector $462_2$ with screw hook 468A. A third wire $470_3$ electrically couples electrical connector $464_1$ with screw hook 468B whereas a fourth wire $470_4$ electrically couples electrical connector $464_2$ with screw hook 468B. Female coupling extension 458 is hollow, as shown by a line 460, such that it can be placed over male coupling extension 422, as shown by an arrow 474. Double lead connector 450 narrows at the distal end of female coupling extension 458 and splits into first lead 454A and second lead 454B, as shown by an arrow 472. Pill-sized pacemaker system 420 is shown having two electrical connectors in each electrical connector set, which can be used in bipolar pacing in a dual lead system. However it is noted that pill-sized pacemaker system 420 can also include only a single electrical connector in each electrical connector set in the male and female coupling extensions (not shown) for unipolar pacing.

Each one of magnetic discs 426 and 456 can be a neodymium magnet or other type of strong permanent magnet which is biocompatible. Once female coupling extension 458 is positioned over male coupling extension 432, magnetic discs 426 and 456 are coupled together via the magnetic force thereby firmly coupling pill-sized pacemaker 422 with double lead connector 450. Electrical connectors $434_1$, $434_2$, $436_1$ and $436_2$ are aligned such that they make electrical contact with electrical connectors $464_1$, $464_2$, $462_1$ and $462_2$ respectively when female coupling extension 458 is positioned over male coupling extension 432. Plurality of drainage channels 466 enable any blood present in female coupling extension 458 to escape when female coupling extension 458 is positioned over male coupling extension 432. Once pill-sized pacemaker 422 and double lead connector 450 are coupled together, the electronics (not shown) in body 424 are electrically coupled with screw hook 428 as well as screw hooks 468A and 468B, enabling signals to be sensed and electric shocks to be delivered via any one of screw hooks 428, 468A or 468B, via a combination of them or via all of them. Pill-sized pacemaker system 420 is substantially similar to pill-sized pacemaker system 350 (FIG. 5), having a similar coupling mechanism between the pill-sized pacemaker and the lead connector, however pill-sized pacemaker system 420 shows how using a single magnetic coupler between a male and female coupling extension (magnetic discs 426 and 456), two leads can be coupled simultaneously with a pill-sized pacemaker. As explained above, screw hook 428 is positioned in the right ventricle of the heart whereas screw hooks 468A and 468B can be positioned in the right atrium, attached to the HIS bundle, the SA node, the AV node, the coronary sinus or even the left ventricle or left atrium via a puncture (not shown) between the left side and right side of the heart. For example, using the double lead connector as shown in FIG. 6, one of screw hooks 468A and 468B can be screwed into the AV node whereas the other one of screw hooks 468A and 468B can be screwed into the coronary sinus, or via a puncture, into the left ventricle. In such an embodiment, once the pill-sized pacemaker is screwed into the right ventricle, the insertion tool used to insert the pill-sized pacemaker is used to bring the double lead connector to the right atrium wherein one of the leads is fastened to the AV node via its screw hook. The insertion tool may then be used to couple the other lead to a different location within the right atrium or it can be used to create a puncture to the coronary sinus or the left ventricle and then used to screw the other lead in. The insertion tool is then removed from the patient and a second insertion tool, as described above in FIGS. 3A-3D, is then used to guide connector end 452 via the tricuspid valve into the right ventricle and is used to align the magnetic discs together between the male and female coupling extensions. It is noted that FIG. 6 has been described showing a double lead connector however the design shown can be easily extended to a multiple lead connector having three or more leads. In all the embodiments shown of the disclosed technique, the magnetic coupling between the male coupling extension and the female coupling extension is only executed once the screw hooks of the pill-sized pacemaker and the lead connector, or lead connectors in the case of a multiple lead connector, are firmly attached to the heart.

It will be appreciated by persons skilled in the art that the disclosed technique is not limited to what has been particularly shown and described hereinabove. Rather the scope of the disclosed technique is defined only by the claims, which follow.

The invention claimed is:

1. Pill-sized pacemaker system, comprising:
a pill-sized pacemaker having a distal end and a proximal end, said distal end comprising a first screw hook and said proximal end comprising a first magnetic coupler; and
a lead connector having a distal end and a proximal end, said distal end comprising a second screw hook and said proximal end comprising a second magnetic coupler,
each one of said first magnetic coupler and said second magnetic coupler being disc-shaped and comprising at least one respective depth-wise electrode,
wherein said first screw hook is for screwing said pill-size pacemaker to a first inner heart tissue and for sensing at least one signal from said first inner heart tissue;
wherein said second screw hook is for screwing said lead connector to a second inner heart tissue and for sensing at least one signal from said second inner heart tissue;
wherein said pill-sized pacemaker and said lead connector are electrically coupled via each one of said at least one respective depth-wise electrode of said first magnetic coupler and said second magnetic coupler when said first magnetic coupler and said second magnetic coupler are magnetically coupled.

2. The pill-sized pacemaker system according to claim 1, said pill-sized pacemaker comprising:
a body; and
a plurality of hooks, for providing further support for coupling said pill-size pacemaker to said first inner heart tissue,
said body comprising:
electronics, for monitoring at least one heart signal and operating said pill-sized pacemaker; and
a power supply, coupled with said electronics, for powering said electronics and for providing power for at least one electric shock,
wherein said first screw hook and said plurality of hooks are coupled with said body at said distal end;
wherein said first magnetic coupler is coupled with said body at said proximal end;
wherein said body has a cylindrical shape; and
wherein said electronics determines if and when said at least one electric shock should be administered.

3. The pill-sized pacemaker system according to claim 2, said body further comprising:
at least one capacitor, coupled with said power supply and said electronics, for providing at least one high voltage electric shock; and
a receiver-transmitter, for receiving and transmitting signals wirelessly.

4. The pill-sized pacemaker system according to claim 1, said lead connector further comprising a lead wire coupling said second screw hook with said second magnetic coupler.

5. The pill-sized pacemaker system according to claim 1, wherein said first magnetic coupler and said second magnetic coupler are made from a biocompatible strong permanent magnet.

6. The pill-sized pacemaker system according to claim 5, wherein said biocompatible strong permanent magnet is a neodymium magnet.

7. The pill-sized pacemaker system according to claim 2, wherein said first screw hook is also for providing said at least one electric shock to said first inner heart tissue and wherein said second screw hook is also for providing said at least one electric shock to said second inner heart tissue.

8. The pill-sized pacemaker system according to claim 2, said pill-sized pacemaker further comprising a rate sensor, for enabling rate responsive pacing of said pill-sized pacemaker.

9. Pill-sized pacemaker system, comprising:
a pill-sized pacemaker having a distal end and a proximal end, said distal end comprising a first screw hook and said proximal end comprising a first magnetic coupler and a male coupling extension; and
a lead connector having a distal end and a proximal end, said distal end comprising a second screw hook and said proximal end comprising a second magnetic coupler and a female coupling extension,
said male coupling extension comprising at least one electrical connector and said female coupling extension comprising at least one respective electrical connector,
each one of said first magnetic coupler and said second magnetic coupler being disc-shaped,
wherein said first screw hook is for screwing said pill-size pacemaker to a first inner heart tissue and for sensing at least one signal from said first inner heart tissue;
wherein said second screw hook is for screwing said lead connector to a second inner heart tissue and for sensing at least one signal from said second inner heart tissue; and
wherein said pill-sized pacemaker and said lead connector are electrically coupled via said at least one electrical connector of said male coupling extension and said at least one respective electrical connector of said female coupling extension when said female coupling extension is positioned over said male coupling extension and said first magnetic coupler is magnetically coupled with said second magnetic coupler.

10. The pill-sized pacemaker system according to claim 9, said pill-sized pacemaker comprising:
a body; and
a plurality of hooks, for providing further support for coupling said pill-size pacemaker to said first inner heart tissue,
said body comprising:
electronics, for monitoring at least one heart signal and operating said pill-sized pacemaker; and
a power supply, coupled with said electronics, for powering said electronics and for providing power for at least one electric shock,
wherein said first screw hook and said plurality of hooks are coupled with said body at said distal end;
wherein said first magnetic coupler is coupled with said body at said proximal end;
wherein said body has a cylindrical shape; and
wherein said electronics determines if and when said at least one electric shock should be administered.

11. The pill-sized pacemaker system according to claim 10, said first magnetic coupler comprising a first magnetic disc having a hole through which said male coupling extension is coupled with said body, wherein said at least one electrical connector is electrically coupled with said electronics.

12. The pill-sized pacemaker system according to claim 11, wherein said first magnetic disc is a biocompatible strong permanent magnet.

13. The pill-sized pacemaker system according to claim 9, said second magnetic coupler comprising a second magnetic disc and said female coupling extension comprising a plurality of draining channels, wherein said female coupling extension is hollow and wherein said at least one respective electrical connector is electrically coupled with said second screw hook.

14. The pill-sized pacemaker system according to claim 13, wherein said second magnetic disc is a biocompatible strong permanent magnet.

15. Pill-sized pacemaker system, comprising:
a pill-sized pacemaker having a distal end and a proximal end, said distal end comprising a first screw hook and said proximal end comprising a first magnetic coupler and a male coupling extension; and
a multiple lead connector having at least two distal ends and a proximal end, each one of said at least two distal ends comprising a respective screw hook and said proximal end comprising a second magnetic coupler and a female coupling extension,
said male coupling extension comprising at least two electrical connectors and said female coupling extension comprising at least two respective electrical connectors,
each one of said first magnetic coupler and said second magnetic coupler being disc-shaped,
wherein said first screw hook is for screwing said pill-size pacemaker to a first inner heart tissue and for sensing at least one signal from said first inner heart tissue;
wherein each said respective screw hook of said multiple lead connector is for screwing each one of said at least two distal ends to a respective at least second inner heart tissue and third inner heart tissue and for sensing at least one signal from each one of said respective at least second inner heart tissue and third inner heart tissue; and
wherein said pill-sized pacemaker and said multiple lead connector are electrically coupled via said at least two electrical connectors of said male coupling extension and said at least two respective electrical connectors of said female coupling extension when said female coupling extension is positioned over said male coupling extension and said first magnetic coupler is magnetically coupled with said second magnetic coupler.

16. The pill-sized pacemaker system according to claim 15, said pill-sized pacemaker comprising:
a body; and
a plurality of hooks, for providing further support for coupling said pill-size pacemaker to said first inner heart tissue,
said body comprising:
electronics, for monitoring at least one heart signal and operating said pill-sized pacemaker; and
a power supply, coupled with said electronics, for powering said electronics and for providing power for at least one electric shock,
wherein said first screw hook and said plurality of hooks are coupled with said body at said distal end;
wherein said first magnetic coupler is coupled with said body at said proximal end;
wherein said body has a cylindrical shape; and
wherein said electronics determines if and when said at least one electric shock should be administered.

17. The pill-sized pacemaker system according to claim 16, said first magnetic coupler comprising a first magnetic disc having a hole through which said male coupling extension is coupled with said body, wherein said at least one electrical connector is electrically coupled with said electronics.

18. The pill-sized pacemaker system according to claim 17, wherein said first magnetic disc is a biocompatible strong permanent magnet.

19. The pill-sized pacemaker system according to claim 15, said second magnetic coupler comprising a second magnetic disc and said female coupling extension comprising a plurality of draining channels, wherein said female coupling extension is hollow and wherein each one of said at least two respective electrical connectors is electrically coupled with a respective one of said respective screw hook of said at least two distal ends.

20. The pill-sized pacemaker system according to claim 19, wherein said second magnetic disc is a biocompatible strong permanent magnet.

21. Method for placement of a pill-sized pacemaker system in the heart of a patient, said pill-sized pacemaker system comprising a pill-sized pacemaker having a first distal end and a first proximal end, said first distal end comprising a first screw hook and said first proximal end comprising a first magnetic coupler, a lead connector having at least one second distal end and a second proximal end, each one of said at least one second distal end comprising a respective second screw hook and said second proximal end comprising a second magnetic coupler, a first insertion tool and a second insertion tool, wherein said pill-sized pacemaker and said lead connector are electrically coupled when said first magnetic coupler and said second magnetic coupler are magnetically coupled, comprising the procedures of:
   making an incision in a right femoral vein of said patient;
   guiding a guidewire from said incision to a first desired position in said heart;
   coupling said pill-sized pacemaker to said first insertion tool;
   guiding said first insertion tool over said guidewire to said first desired position;
   turning said first insertion tool to twist said first screw hook into said first desired position;
   removing said first insertion tool;
   guiding said guidewire to a second desired position in said heart;
   coupling said lead connector to said first insertion tool;
   guiding said first insertion tool over said guidewire to said second desired position;
   turning said first insertion tool to twist said respective second screw hook into said second desired position;
   removing said first insertion tool;
   guiding said second insertion tool over said guidewire to said second desired position and grabbing said second magnetic coupler;
   guiding said second magnetic coupler to said first desired position;
   turning said second insertion tool to align said second magnetic coupler with said first magnetic coupler;
   moving said second magnetic coupler in close proximity to said first magnetic coupler using said second insertion tool such that said second magnetic coupler is magnetically coupled with said first magnetic coupler;
   removing said second insertion tool;
   removing said guidewire; and
   suturing up said incision.

22. The method for placement of a pill-sized pacemaker system according to claim 21, wherein said first desired position is a right ventricle of said heart.

23. The method for placement of a pill-sized pacemaker system according to claim 21, wherein said second desired position is selected from the list consisting of:
   a right atrium of said heart;
   an atrioventricular (AV) node of said heart;
   a sinoatrial (SA) node of said heart;
   a HIS bundle of said heart;
   a coronary sinus of said heart;
   a left atrium of said heart; and
   a left ventricle of said heart.

* * * * *